US00PP36186P2

(12) United States Plant Patent
Zaiger et al.

(10) Patent No.: US PP36,186 P2
(45) Date of Patent: Oct. 8, 2024

(54) ***INTERSPECIFIC PRUNUS* TREE NAMED 'Sweet Pixie 6'**

(50) Latin Name: *Interspecific Prunus species*
Varietal Denomination: Sweet Pixie 6

(71) Applicants: Gary Neil Zaiger, Modesto, CA (US); Leith Marie Gardner, Modesto, CA (US)

(72) Inventors: Gary Neil Zaiger, Modesto, CA (US); Leith Marie Gardner, Modesto, CA (US)

( * ) Notice: Subject to any disclaimer, the term of this patent is extended or adjusted under 35 U.S.C. 154(b) by 0 days.

(21) Appl. No.: 18/445,745

(22) Filed: Jan. 12, 2024

(51) Int. Cl.
*A01H 5/08* (2018.01)
*A01H 6/74* (2018.01)

(52) U.S. Cl.
USPC ..... Plt./180

(58) Field of Classification Search
USPC ..... Plt./180
See application file for complete search history.

*Primary Examiner* — Karen M Redden
*Assistant Examiner* — Zachariah Allan Kay

(57) ABSTRACT

A new and distinct variety of interspecific (*Prunus* species) tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, California, with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of small to medium size, yellow flesh fruit.
3. Fruit with excellent flavor and eating quality.
4. Fruit with a high degree of attractive red skin color.
5. Fruit with good storage and shipping ability.

1 Drawing Sheet

Botanical designation: Interspecific *Prunus* species.
Variety denomination: 'SWEET PIXIE 6'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, California.

PRIOR VARIETIES

Among the existing varieties of interspecific and apricot trees, which are known to us, and mentioned herein, 'Sweet Pixie' Interspecific (U.S. Plant Pat. No. 23,211) , 'PA7221-1' (U.S. Plant Pat. No. 7,035) , 'Black Kat' Interspecific (U.S. Plant Pat. No. 13,134), and the proprietary non-patented apricot seedling selections '384LD362' and '71EB628'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, California from a first generation cross between 'Sweet Pixie' Interspecific (U.S. Plant Pat. No. 23,211) and our proprietary non-patented apricot variety '384LD362'. The pollen parent '384LD362' originated from the cross of our proprietary non-patented apricot seedling '71EB628' and 'PA7221-1' Apricot (U.S. Plant Pat. No. 7,035). A large number of these first generation seedlings were grown and budded onto older established trees of 'Nemaguard' Rootstock (non-patented) to accelerate rapid fruit production. Under close and careful observation we recognized the desirable tree and fruit characteristics of the present seedling and selected it in 2009 for additional asexual propagation and commercialization.

ASEXUAL REPRODUCTION OF THE VARIETY

In 2009 asexual reproduction of the new and distinct variety of interspecific tree was by budding to 'Nemaguard' Rootstock (non-patented), as performed by us in our experimental orchard located near Modesto, California, and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of small to medium size, freestone fruit with an attractive red skin color. The fruit is further characterized by its firm, yellow flesh, excellent flavor and eating quality and having a good storage and shipping ability. In comparison to its seed parent 'Sweet Pixie' Interspecific (U.S. Plant Pat. No. 23,211) the fruit of the new variety is approximately 49 days later in maturity. In comparison to its proprietary non-patented apricot pollen parent ('384LD362') the fruit of the new variety is approximately 68 days later in maturity and has glabrous skin compared to pubescent. In comparison to the commercial variety 'Black Kat' Interspecific (U.S. Plant Pat. No. 13,134) the fruit of the new variety is approximately 20 days earlier in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 14 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 14 year old specimens grown near Modesto, California, with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 12 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 800 hours at or below 45° F.

Trunk:

*Size*.—Medium, average circumference 45.7 cm at 25.4 cm above ground ,on a 14 year old tree.

*Stocky*.—Medium stocky.

*Texture*.—Medium shaggy, roughness increases with age of tree.

*Color*.—Varies from 5Y 5/2 to 7.5Y 7/2.

Branches:

*Size*.—Medium. Average circumference 14.5 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 63 in a 25.8 square cm area. Average length 3.5 mm. Average width 1.4 mm. Color varies from 2.5Y 6/8 to 5Y 7/6.

*Color*.—New growth varies from 5GY 5/8 to 5GY 4/6. Mature growth varies from 7.5YR 2/4 to 10YR 4/2, varies with age of growth.

Leaves:

*Size*.—Medium to large. Average length 138.8 mm. Average width 42.1 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 14.4 mm. Average width 1.6 mm. Longitudinally grooved. Surface-glabrous. Color varies from 5GY 4/6 to 7.5R 2/6.

*Glands*.—Type — globose. Size — small. Glands: Average length 0.5 mm. Average diameter 0.3 mm. Average number 2, varies from 1 to 3. Located primarily on the base of the leaf blade and upper portion of the petiole. Color — 5GY 6/6.

*Stipules*.—Average number 2 per leaf. Average length 9.2 mm. Edges — pectinate. Color varies from 5GY 5/6 to 5GY 5/8.

*Color*.—Upper surface varies from 5GY 4/8 to 7.5GY 3/4. Lower surface varies from 5GY 5/6 to 5GY 4/4. Midvein color varies from 2.5GY 6/6 to 5GY 5/6.

Flower buds:

*Size*.—Medium. Average length 10.4 mm. Average diameter 6.1 mm.

*Hardiness*.—Hardy with respect to California winters.

*Density*.—Very dense.

*Form*.—Conical, becoming elongated just before opening.

*Pedicel*.—Average length 11.0 mm. Average width 0.7 mm. Surface — glabrous. Color varies from 2.5GY 6/6 to 2.5GY 6/8.

*Color*.—N 9.5/(white).

*Number of buds per spur*.—Average number 10, varies from 7 to 12.

Flowers:

*Blooming period*.—Date of First Bloom Feb. 27, 2023. Date of Petal Fall Mar. 8, 2023, varies slightly with climatic conditions.

*Size*.—Medium. Average height 10.1 mm. Average diameter 17.4 mm.

*Petals*.—Number — normally 5, alternately arranged to sepals. Size — medium. Average length 10.9 mm. Average width 5.1 mm. Form — elliptical. Arrangement — free. Petal apex — rounded. Petal base — truncate. Margin — sinuate. Both upper and lower surfaces glabrous. Color N 9.5/(white).

*Sepals*.—Number — normally 5, alternately arranged to petals. Size — medium to large. Average length 4.1 mm. Average width 3.1 mm. Shape — triangular. Margin — entire. Sepal apex triangular. Both upper and lower surfaces glabrous. Color — upper surface varies from 2.5GY 6/8 to 5GY 6/6. Lower surface varies from 5GY 6/8 to 5GY 5/6.

*Stamens*.—Average number per flower 28, varies from 27 to 30. Average filament length 7.4 mm. On average, the stamens are even with the height of the petals. Filament color N 9.5/(white). Anther color varies from 5Y 8/10 to 5Y 7/8.

*Pollen*.—Present, self-sterile, pollinator required. Color varies from 2.5Y 7/10 to 5Y 7/10.

*Pistil*.—Number — normally one. Average length 7.2 mm. Position of stigma an average of 1.5 mm below the anthers. Surface — glabrous. Color varies from 10Y 8/6 to 2.5GY 8/6.

*Fragrance*.—Heavy aroma.

*Color*.—N 9.5/(white).

*Pedicel*.—Average length 11.8 mm. Average width 0.8 mm. Surface — glabrous. Color varies from 2.5GY 6/6 to 2.5GY 6/8.

*Number flowers per flower bud*.—Average number 2, varies from 1 to 3.

Fruit:

*Maturity when described*.—Firm ripe and ready for consumption.

*Date of first picking*.—Aug. 15, 2023.

*Date of last picking*.—Aug. 25, 2023, varies slightly with climatic conditions.

*Size*.—Small to medium. Average diameter axially 40.4 mm. Average transversely in suture plane 41.5 mm. Average weight 48.3 grams, varies slightly with fertility of the soil, amount of thinning and climatic conditions.

*Form*.—Globose.

*Suture*.—Nearly smooth, some fruit with slight suture, extends from base to apex.

*Ventral surface*.—Nearly smooth.

*Apex*.—Nearly rounded.

*Base*.—Very slightly retuse.

*Stem cavity*.—Rounded to slightly elongated in suture plane. Average depth 4.7 mm. Average diameter 2.7 mm.

Stem:

*Size*.—Large. Average length 19.0 mm. Average diameter 1.2 mm.

*Color*.—Varies from 2.5GY 7/8 to 2.5GY 6/6.

Flesh:

*Ripens*.—Evenly.

*Texture*.—Firm, meaty.

*Fibers*.—Few, small, tender.

*Firmness*.—Firm, comparable to other commercial interspecific varieties.

*Aroma*.—Moderate aroma.

*Amydgalin*.—Undetected.

*Eating quality*.—Excellent.

*Flavor*.—Excellent, with a good balance between acid and sugar.

*Juice*.—Moderate amount, enhances flavor.

*Acidity*.—Not available.

*Brix*.—Average Brix 26.9°, varies slightly with amount of fruit per tree and climatic conditions.

*Color*.—Varies from 2.5Y 8/10 to 5Y 8/8.

*Pit cavity*.—Average length 21.5 mm. Average width 16.4 mm. Average depth 5.7 mm. Color varies from 10YR 7/10 to 10YR 6/10.

Skin:

*Thickness*.—Medium.

*Surface*.—Smooth.

*Bloom*.—Moderate amount, complete coverage.

*Tendency to crack*.—None.

*Color*.—Ground color varies from 7.5Y 8/6 to 10Y 8/4.-Overspread with 5R 2/4 to 7.5R 3/8. Very small, randomly spaced areas of ground color exposed to give a speckling pattern to surface areas.

*Tenacity*.—Tenacious to the flesh.

*Astringency*.—Slight to none.

Stone:

*Type*.—Freestone, light adherence to flesh.

*Size*.—Medium. Average length 19.9 mm. Average width 14.9 mm. Average thickness 9.3 mm.

*Form*.—Ovoid.

*Base*.—Flat.

*Apex*.—Pointed. Average length 1.5 mm.

*Surface*.—Slightly pitted throughout, pits vary from round to elongated.

*Sides*.—Unequal, one side extending slightly further from the suture plane.

*Ridges*.—Small, extending from base to apex.

*Tendency to split*.—None.

*Color*.—Varies from 7.5YR 4/6 to 10YR 5/8, when dry.

Kernel:

*Size*.—Small. Average length 12.9 mm. Average width 8.1 mm. Average depth 5.4 mm.

*Form*.—Ovate.

*Viability*.—Viable, complete embryo development.

*Skin color*.—Varies from 10YR 6/8 to 10YR 5/8.

Use:

*Dessert*.—Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, California, no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, California.

The invention claimed is:

1. A new and distinct variety of interspecific (*Prunus* species) tree named 'Sweet Pixie 6', substantially as illustrated and described.

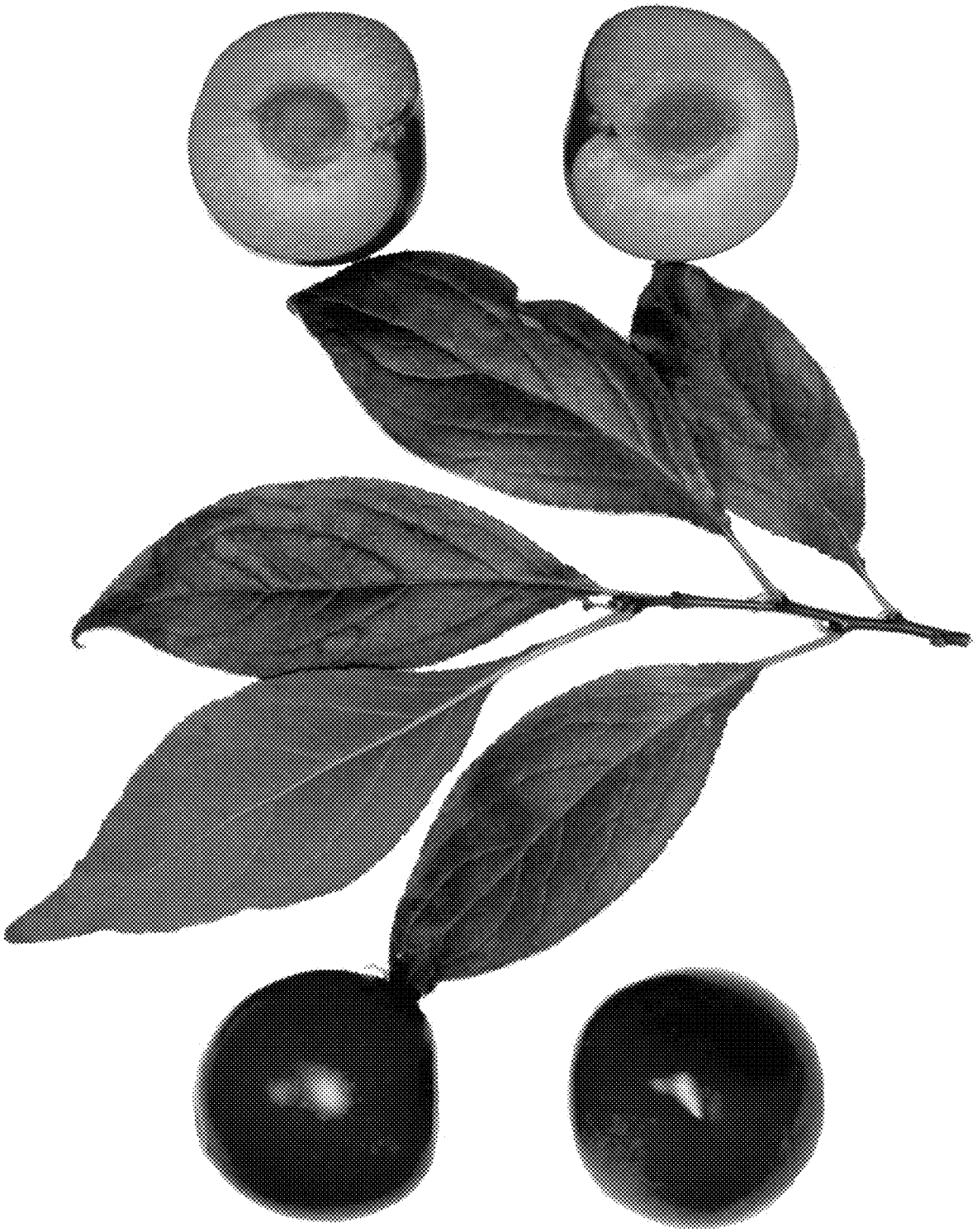

* * * * *